(12) United States Patent
Barbeau et al.

(10) Patent No.: US 7,934,425 B2
(45) Date of Patent: May 3, 2011

(54) NON-DESTRUCTIVE ULTRASOUND INSPECTION METHOD AND MEASUREMENT PROBE FOR IMPLEMENTING THE METHOD

(75) Inventors: Pierre Barbeau, Blagnac (FR); Guillaume Ithurralde, Colomiers (FR)

(73) Assignee: Airbus France, Toulouse (FR)

( * ) Notice: Subject to any disclaimer, the term of this patent is extended or adjusted under 35 U.S.C. 154(b) by 599 days.

(21) Appl. No.: 11/930,276

(22) Filed: Oct. 31, 2007

(65) Prior Publication Data

US 2008/0148855 A1 Jun. 26, 2008

(51) Int. Cl.
*G01N 29/06* (2006.01)
(52) U.S. Cl. .............................. 73/602; 73/625; 73/628
(58) Field of Classification Search .................... 73/602, 73/626, 628, 625
See application file for complete search history.

(56) References Cited

U.S. PATENT DOCUMENTS

| | | | |
|---|---|---|---|
| 4,317,369 A | 3/1982 | Johnson | |
| 4,831,601 A * | 5/1989 | Breimesser et al. | 367/88 |
| 5,261,408 A * | 11/1993 | Maslak et al. | 600/447 |
| 5,563,346 A * | 10/1996 | Bartelt et al. | 73/626 |
| 5,601,083 A * | 2/1997 | Anderson | 600/443 |
| 5,992,235 A | 11/1999 | Fischer et al. | |
| 6,055,861 A * | 5/2000 | Banta et al. | 73/626 |
| 6,443,011 B1 | 9/2002 | Schulze et al. | |
| 6,582,367 B1 * | 6/2003 | Robinson et al. | 600/443 |
| 6,792,808 B1 | 9/2004 | Batzinger et al. | |
| 2002/0073781 A1 | 6/2002 | Hashimoto | |
| 2005/0000279 A1 | 1/2005 | Yogeswaren | |

* cited by examiner

*Primary Examiner* — Hezron Williams
*Assistant Examiner* — Rose M Miller
(74) *Attorney, Agent, or Firm* — Perman & Green, LLP (57) ABSTRACT

A method for inspecting a part by a non-destructive ultrasound inspection, the part is immersed in an acoustic wave conducting medium and an incident ultrasound wave having a wide beam of section $\Sigma$ is emitted into the ultrasound-conducting medium towards the part. The characteristics of the waves reflected by faces of the part to be inspected are measured on at least a small section $\sigma$, the characteristic dimensions of which are substantially less than those of the section $\Sigma$. The location of the section or sections $\sigma$ is determined such that, despite the possible variations of the position of the part and the relative slopes of its faces, the section $\sigma$ is always located in the volumes passed through by the reflected waves, for example substantially in an area close to the axis of the incident beam when the incident beam is controlled to be oriented substantially in a direction perpendicular to a face of the part.

8 Claims, 5 Drawing Sheets

NON-DESTRUCTIVE ULTRASOUND INSPECTION METHOD AND MEASUREMENT PROBE FOR IMPLEMENTING THE METHOD

BACKGROUND

1. Field

The disclosed embodiments relate to the field of non-destructive inspection of parts by ultrasound reflection.

In particular, the disclosed embodiments relate to a method suitable for automatically inspecting non-flat areas or areas with non-parallel faces of parts such as parts made of composite materials.

2. Brief Description

The general principle of non-destructive ultrasound inspection of structural parts is these days well known and widely implemented.

This principle consists in placing all or some of a part to be inspected in an immersion medium that is a good conductor of ultrasound acoustic waves, for example by immersing the part in a tank or by locally creating immersion conditions by means of a water box or even by creating a fluid immersion film by the continuous application of the fluid, this immersion medium being more often than not water because of its excellent acoustic wave conduction characteristics, its low chemical aggressivity for the inspected parts and its negligible cost, in emitting ultrasound waves towards points of the part to be inspected and collecting the reflected waves in the form of echoes from the part. In practice, the waves are reflected by the different interfaces of the part each time a discontinuity provokes a reflection of a portion of the energy of the emitted acoustic wave. These discontinuities are more often than not a wall of the part, at the interface with the immersion medium or with a joined part, a defect in the material of the part. The reflected waves are also influenced by characteristics of the material passed through. Thus, for example, its porosity can be assessed by measuring the attenuation of the waves reflected by a rear interface, provided that the waves reflected by said rear interface reach measurement sensors.

The ultrasound acoustic wave is propagated in the medium in which the part is immersed and in the material of the part and, according to the known laws of propagation and reflection, each time the incident acoustic wave encounters a discontinuity or a variation of the characteristics, a portion of the incident wave is transmitted and another portion is reflected.

The energies and the phases of the transmitted and reflected waves make it possible, after signal measurements and processing, to determine certain characteristics of the part being inspected.

When applied to parts made of composite materials, the non-destructive ultrasound inspection can be used to detect internal defects in the parts such as, for example, delaminations or porosity characteristics which are essential parameters for parts subject to stresses in their use.

Figure 1A:
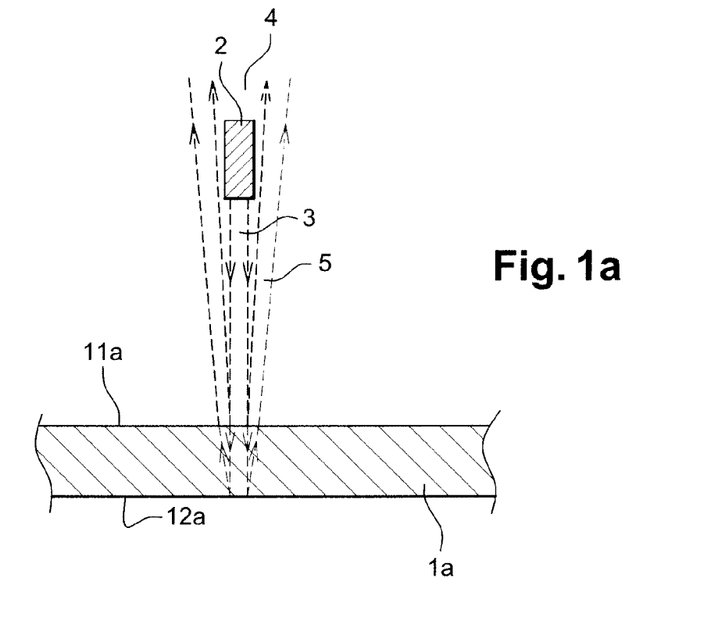
FIGS. 1a, 1b and 1c: already mentioned, known non-destructive ultrasound inspection situations, with the part and probe positioned ideally relative to each other (FIG. 1a), in a situation with an inclined part (FIG. 2a) and in a situation with a part with non-parallel faces (FIG. 1c)

The general principle of the means used for these non-destructive tests is illustrated by FIG. 1a.

A probe 2 emits in an emission mode an ultrasound wave 3 towards a part to be inspected 1a. A surface 11a of the part 1a which receives the incident wave 3 reflects a portion of this incident wave in the form of a first reflected wave 4 which is measured by the probe 2 then working in reception mode. Another portion of the incident wave which penetrates into the material of the part 1a is in turn reflected by another surface 12a of the part and forms a second reflected wave 5 which is also able to be measured by the probe 2 working in reception mode.

To perform this type of measurement, probes that emit the incident waves and that measure the reflected signals are normally used. These probes more often than not use transducers based on piezoelectric technologies which are perfectly suited to the frequencies of the ultrasounds used and which have the advantage of being able to measure the reflected waves with the same transducers as those that generate the incident wave.

However, the need for high spatial resolution means selecting directional sensors, which sensors are ineffective when one of the interfaces of the part, an input or bottom interface, is not normal to the direction of propagation of the incident acoustic wave.

Figure 1B:
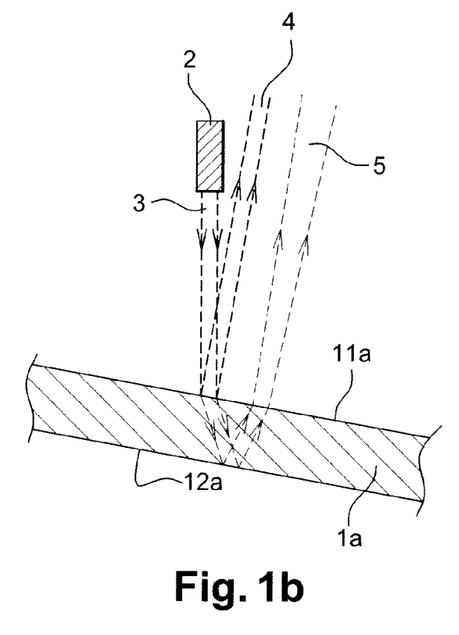

As illustrated in FIG. 1b, if the surface 11a of the part 1a is not perfectly perpendicular to the direction of the incident wave 3, the reflected waves 4 and 5 will not be directed efficiently to the probe and the latter will not be able to return a satisfactory measurement. This phenomenon is not too problematic when the probe is almost in contact with the surface of the part, as in the case of probes held by an operator, but proves critical when the probe is distant from the surface of the part which is normally the case in automated inspection devices with an immersed part. The probe in these devices is located at a distance more often than not of between 3 and 12 centimeters and a very small relative positioning deviation between the part and the probe is sufficient to disturb the measurement, one degree of angular deviation being sufficient to lower the amplitudes of the received signals by several decibels.

Figure 1C:
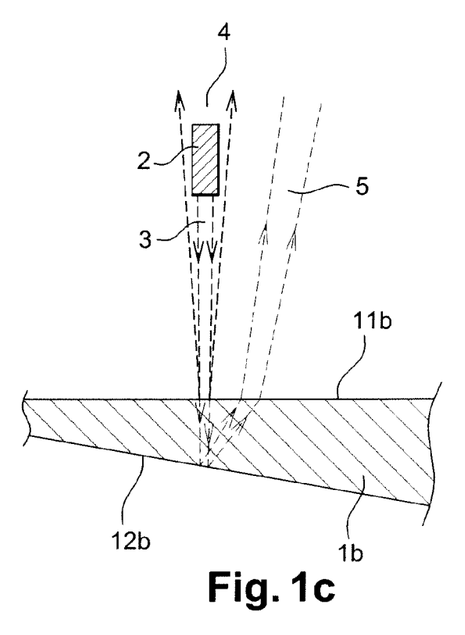

When, as represented in FIG. 1c, the part 1b has non-parallel faces 11b, 12b, a correct relative positioning of the probe and relative to the front face 11b of the part is no longer sufficient to ensure a correct measurement of the wave 5 reflected by the rear face 12b and, in this case, the existing devices often require further inspections to be carried out.

Thus, the highly directional probes, using a sensor or a linear array of sensors implemented with a sequential sweep mode to orient the axis of the ultrasound beam, are always difficult to implement because of their very low tolerances to the positioning deviations relative to the parts to be inspected, particularly in automated inspection processes and in particular when the parts to be inspected have a complex or disturbed geometry.

SUMMARY

To overcome the constraints imposed by the severe relative positioning tolerances between the probes and the parts to be inspected, and to simplify the means of automating non-destructive ultrasound inspections of complex parts, the inventive method consists in emitting an ultrasound wave, called incident wave, into a medium recognized for its ultrasound conduction qualities, towards the part, immersed in said ultrasound-conducting medium, and in measuring characteristics of waves reflected by faces of the part to be inspected to deduce therefrom characteristics of said part, and, in order for the measurement to be little influenced by relative positioning deviations of the measurement means and of the part:

the incident wave is emitted with a beam oriented along an axis and comprising a first section $\Sigma$, the dimensions of which are dimension characteristics of the incident beam, and;

the reflected waves are measured on at least one second section $\sigma$, the characteristic dimensions of which are substantially smaller than those of the first section $\Sigma$ in all the dimensions.

Advantageously, to obtain good quality measurements, the location relative to the incident beam of the second section σ on which the reflected waves are measured is chosen such that said section σ remains located in each of the volumes passed through by the reflected waves regardless of the desired position of the part, taking into account uncertainties as to said position and taking into account relative slopes of the faces of the part for which the reflected waves must be measured.

Preferably, to obtain a faster inspection of the part, the reflected waves are measured simultaneously on several second sections σ1, σ2, ... σn.

In a preferred embodiment, the incident beam is oriented substantially perpendicularly to the faces of the part to be inspected and the reflected waves are measured on a second section σ, or on several second sections σ1, ... σn, located close to the axis of the incident wave beam, and, when the faces of the part comprise non-flat surfaces, the incident wave comprises a wavefront configured to ensure an incidence of said incident wave that is normal to a theoretical surface of the part or configured from an ultrasound measurement of a profile of the part being inspected.

Characteristics of the reflected waves, measured on the second sections σ1, ... σn, are, for example, stored for off-line processing or even combined in real time to be viewed or stored.

In order to implement the method efficiently, the disclosed embodiments also relate to an ultrasound probe for emitting an incident ultrasound beam and measuring characteristics of ultrasound waves reflected by a part to be inspected which comprises a first area, called central emission-reception area, comprising at least one element able to emit ultrasounds and to measure characteristics of ultrasounds arriving on said element and a second area extending around the central area, called peripheral emission area, dedicated to the emission of ultrasounds.

Preferably, in order for the deflections of the reflected waves to reach the measurement element or elements of the central area, the peripheral area dedicated to the emission of ultrasounds comprises an active emission surface substantially equal to or greater than three times the active surface of the central emission-reception area.

To carry out the measurement simultaneously at different points of the part to be inspected, the central emission-reception area preferably comprises a matrix of independent elements able to emit ultrasounds and measure ultrasound characteristics. To take account of the shapes of the parts to be inspected and optimize the inspection operations, for example either the matrix of independent elements comprises substantially equal numbers of columns and rows, or the matrix of independent elements comprises a number of rows and a number of columns that are substantially different, or the peripheral area comprises several emission elements able to be controlled separately to configure the incident wavefront.

BRIEF DESCRIPTION OF THE DRAWINGS

The detailed description of the disclosed embodiments is given with reference to the figures which represent:

FIGS. 1a to 4 should be interpreted as sections in a particular arbitrary plane and to reflect a general situation in any direction.

DETAILED DESCRIPTION

A non-destructive ultrasound inspection method for inspecting a part 1a, 1b consists in immersing the part in a medium recognized for its capabilities to ensure the propagation of the ultrasounds, for example water, called immersion liquid, in emitting an ultrasound wave 3, called incident wave, into the immersion liquid towards the part 1a, 1b and in collecting the waves 4, 5, called reflected waves, which are also propagated in the immersion medium after having been reflected by the different faces 11a, 12a, 11b, 12b of the part.

The concept of immersion should be considered here in a broad sense and covers the various techniques that can be used to maintain the continuity of the ultrasound-conducting medium between the means of generating the ultrasounds of the incident wave and the means of measuring the ultrasounds of the reflected waves on the one hand and the part to be inspected on the other hand. The known means include immersion tanks, devices for maintaining a film of the fluid used or even the deposition of a gel in the paste state at the interface between the probes and the part.

Some of said waves 5 are propagated, over a part of their paths, inside the material of the part to be inspected, material whose physical properties are likely to modify certain measurable characteristics of the reflected waves.

Examining the characteristics, in particular the intensities and propagation times of the waves reflected by the different faces of the part and by different points of said faces, makes it possible, by known signal processing methods, to determine geometrical characteristics of the part, for example defects in its structure revealed by discontinuities of the characteristics of the material of the part, and to determine physical characteristics of the part, for example the porosity of the material of the part.

According to the method, the incident wave 3 is an ultrasound beam of wide section Σ, whose wavefront is oriented to be propagated towards a surface of the part 1a, 1b to be inspected to which is directed said ultrasound beam such that a large surface S of the part receives the incident wave 3, and reflected waves are measured on a small surface a of the wavefronts of the reflected waves 4, 5.

The expressions "large section of the incident wave beam", "large surface S of the part" and "small surface a of the reflected wavefront" should be understood to mean that the surface σ of a reflected wave that is measured, which corresponds to a surface element of the part 1a, 1b to be inspected on one of its faces, is substantially smaller than the surface S of the inspected part receiving the incident ultrasound beam 3 and than the section Σ of the incident wave beam which is of the same order of magnitude as the surface S.

According to the method, when a reflected wave 4, 5 is reflected in a direction substantially different from that expected because of an irregularity of a surface 11a, 12a, 11b, 12b of the part to be inspected, the small surface σ still receives an energy, which can be used by the measurement means, of said wave reflected by said part because of the position of said surface σ chosen to be close to an axis of a wave which would be reflected by a defect-free part and perfectly placed relative to the incident beam and because of the small dimensions of said surface σ relative to the wavelength of the ultrasound wave in the immersion liquid concerned. Said axis is, for example, chosen to be substantially in the center of the section of the reflected wave, but is advantageously offset relative to said center when the predictable deflections of the reflected waves are not symmetrical.

In a preferred embodiment of the method, the incident wave 3 is oriented to be propagated substantially perpendicularly to the faces 11, 11a, 11b, 12, 12a, 12b of the part to be inspected and, in this case, the waves 4, 5 reflected by said faces are propagated substantially in the same direction as the incident wave 3 and in the reverse direction, the measurement on a small surface σ is advantageously carried out close to an axis 31 of the incident beam 3, that is, substantially in the center of the section Σ of the incident beam 3.

Figure 2A:
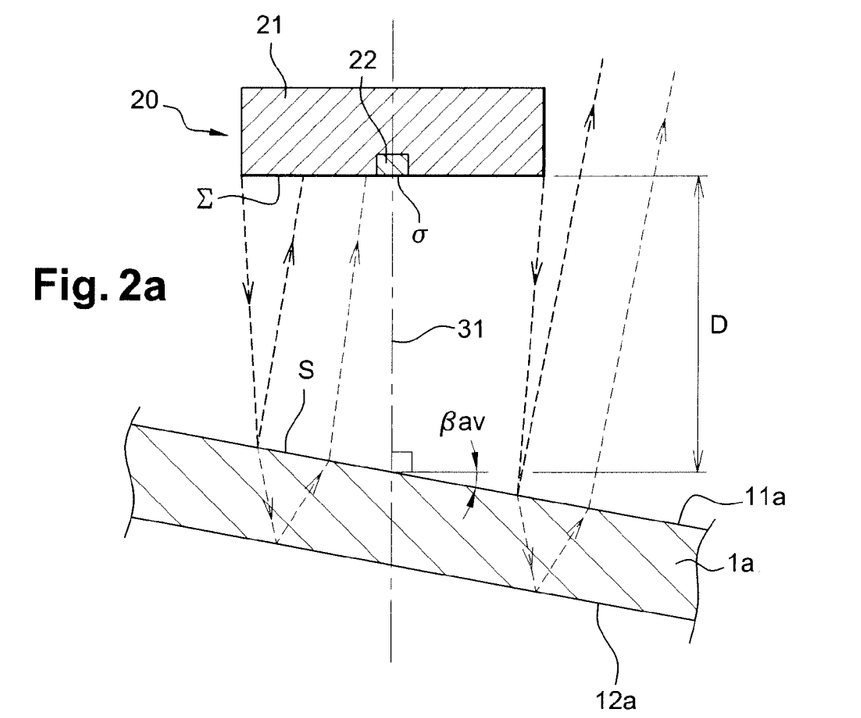
FIGS. 2a, 2b, 2c, 2d: schematic diagram of a measurement according to the disclosed embodiments in the case of a part with parallel faces.
Figure 2B:
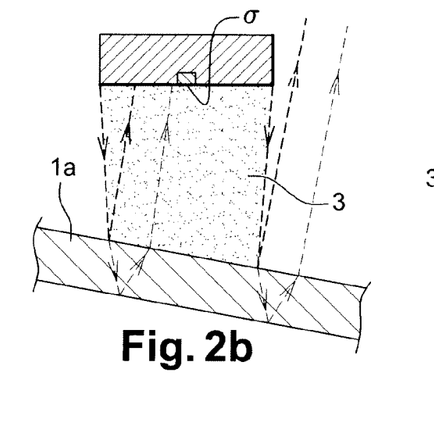

In the example of a measurement illustrated in FIGS. 2a to 2d, a wide incident ultrasound beam 3 of axis 31, represented by a shaded area in FIG. 2b, is emitted towards a surface S of a part 1a. The part 1a is a part whose front and rear faces 11a, 12a, the terms front and rear being used relative to the direction of propagation of the incident wave 3, are substantially parallel but whose normal is offset by angle βav relative to the direction of propagation of the incident wave 3, for example because of a poor relative positioning between the part to be inspected 1a and means 21 of generating the incident beam 3. In FIGS. 2a to 2d, the angle βav is greatly exaggerated compared to a real case for the purposes of illustrating the method.

Figure 2C:
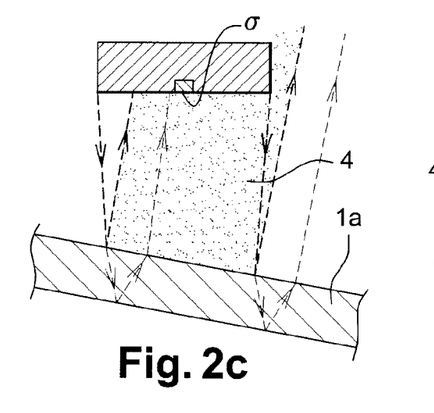

Because of this offset, a priori random, by an angle βav, the reflected wave 4, represented by a shaded area in FIG. 2c, reflected by the surface S of the front face 11a follows a direction that is different from that of the incident wave 3 in accordance with known reflection laws. However, the reflected wave beam 4 is wide, substantially of the same width as the incident wave beam 3, and the quality of the measurement on the small surface σ is not affected by the deflected direction of the reflected beam 4, at least as long as said small measurement surface σ is located in the reflected beam 4, that is, as long as the angle βav remains within limit values, according to the distance D at which the measurement of the reflected wave 4 is performed and the width of the incident beam 3.

Figure 2D:
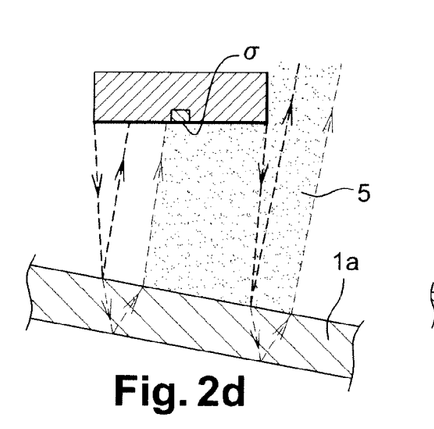

The same applies for the reflected wave 5, represented by a shaded area in FIG. 2d, reflected by the rear face 12a of the part 1a, said wave 5 having also been subjected to the effects of refraction by passing through the front surface 11a between the immersion medium and the material of the part 1a.

As FIG. 2a illustrates, the method makes it possible to measure the characteristics of a part 1a, with parallel faces 11a, 12a, without requiring, as with the known means and methods, the means 20 of generating the ultrasound beam and measuring reflected beams to be positioned very precisely, as in the prior art illustrated in FIGS. 1a and 1b.

Figure 3A:
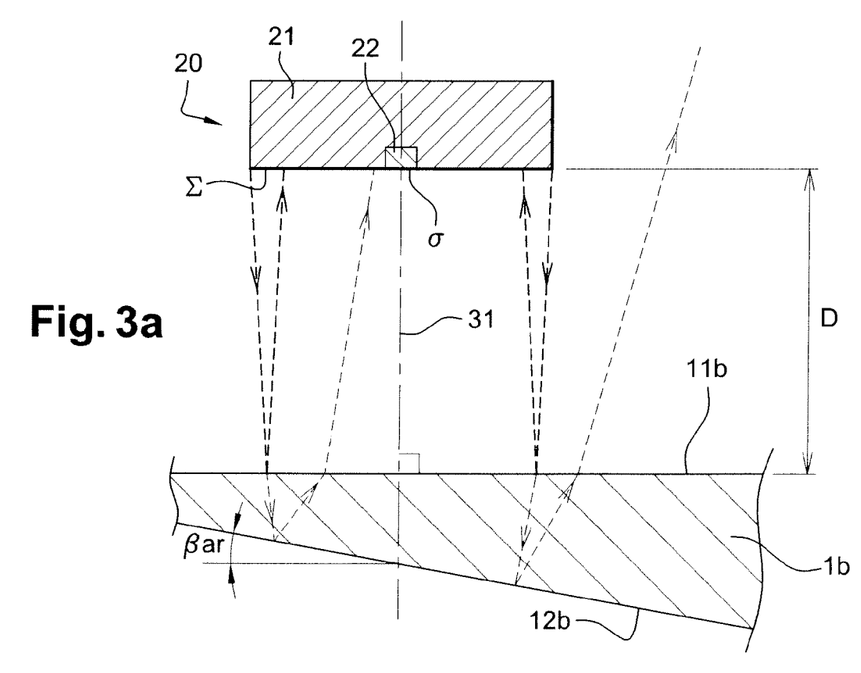
FIGS. 3a, 3b, 3c, 3d: schematic diagram of a measurement according to the disclosed embodiments in the case of a part with non-parallel faces.
Figure 3B:
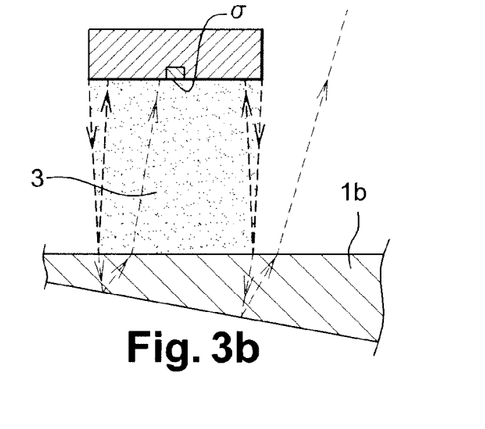

In the measurement example illustrated in FIGS. 3a to 3d, a wide incident ultrasound beam 3, represented by a shaded area in FIG. 3b, is emitted towards a surface S of a part 1b. The part 1b is a part whose front and rear faces 11b and 12b, the terms front and rear being used relative to the direction of propagation of the incident beam, are inclined relative to each other by an angle βar. In this example, the front face is positioned perfectly perpendicularly to the direction of propagation of the incident wave 3 of axis 31 which means that the angle βar substantially corresponds to the angle between the normal to the rear surface 12b and the direction of the incident wave after this wave has passed through the material of the part 1b. Said angle βar corresponds for example to a defect in the part or to a thickness of the part that is variable by construction. In FIGS. 3a to 3d, the angle βar is exaggerated compared to a real case for the purposes of illustrating the method.

Figure 3C:
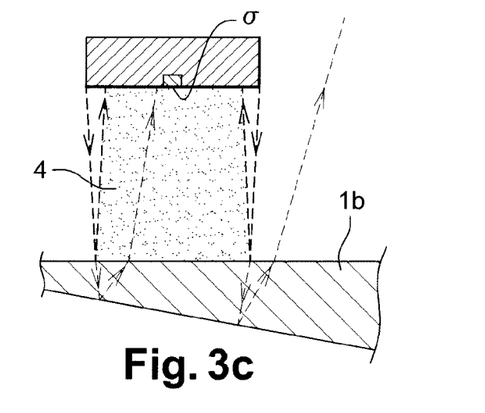

In this case, the reflected wave 4, represented by a shaded area in FIG. 3c, reflected by the front face 11b follows, after reflection on the surface S, the same direction as that of the incident wave 3, in the reverse direction, and is measured with no particular problem on the surface σ which is consequently substantially in the center of the reflected wave 4.

Figure 3D:
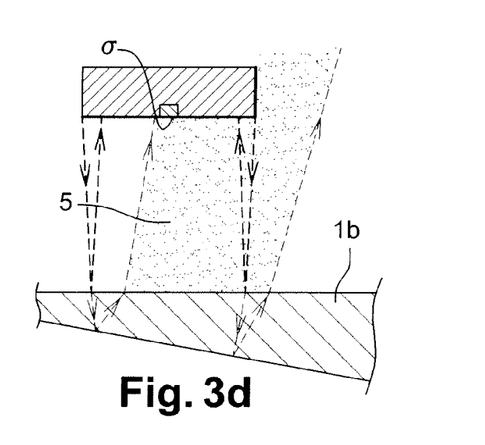

The reflected wave 5, represented by a shaded area in FIG. 3d, reflected by the rear face 12b by a surface S' not shown, equivalent to the surface S of the front face 11b, having been subjected to the effects of refraction by passing through front surface 11b between the immersion medium and the material of the part 1b, is therefore deflected in a way similar to the preceding case when the part 1a had parallel and inclined faces, but in the same way the quality of the measurement on the small surface σ is not affected by the deflected direction of the reflected beam 5, at least as long as said small measurement surface σ is located in the reflected beam 5, that is, as long as the angle βar remains within acceptable values, according to the distance D at which the measurement of the reflected wave 5 is performed and the width of the incident beam 3.

Thus, as FIG. 3a illustrates, the method makes it possible to measure the characteristics of a part 1b, with non-parallel faces 11b, 12b, without requiring, as with the known means and methods, the means 20 of generating the ultrasound beam and of measuring reflected beams to be positioned very precisely, as with the prior art represented in FIGS. 1a and 1c, and to perform different measurements with different positions of the means 20 depending on whether the measurement is performed on the beam reflected by the front face 11b or by the rear face 12b.

To produce an ultrasound image of the part 1, 1a, 1b to be inspected by using the method, the part and the incident beam are displaced relative to each other such that reflected waves from various points of the part having to be inspected are measured on the small surface σ. The sweep of the part 1 by the incident beam is produced by conventional means but, because of the proposed method, it is not necessary to perform a relative positioning of the part and of the means of generating and measuring ultrasound beams that is as precise as with a conventional method.

Figure 4:
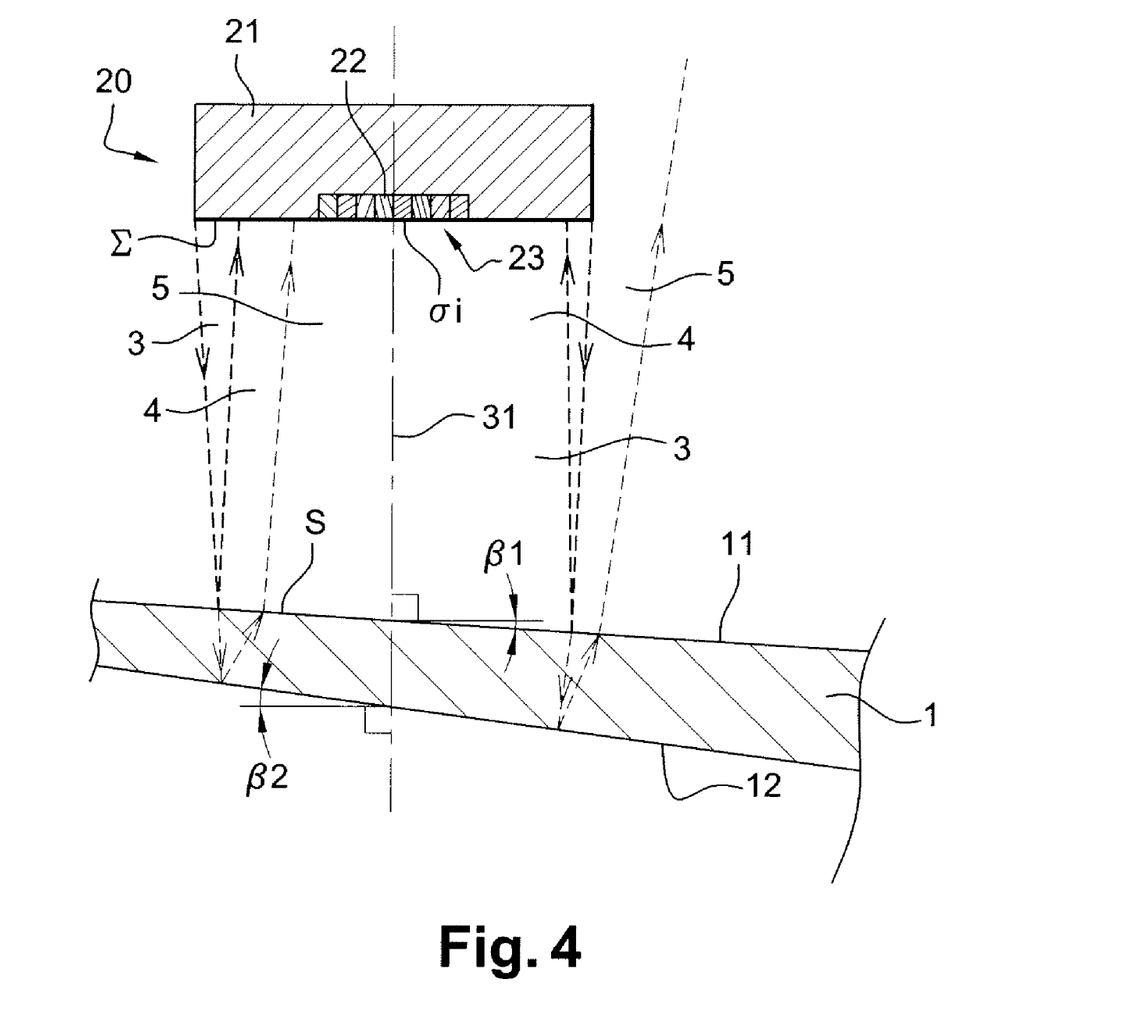
FIG. 4: schematic diagram of a matrix measurement according to the disclosed embodiments.

In a particular embodiment of the method illustrated in FIG. 4, the reflected waves are measured on several small surfaces σi, i=1 to n.

As already described, all the small surfaces σi are positioned such that they receive the waves reflected by the surfaces S and S' of the faces 11, 12 of the part 1 even though these surfaces are likely to reflect the waves in directions that are different from the incident wave because of an alignment defect β1 of the front face 11 and/or of an angle β2 of the rear face 12.

It is thus possible to measure the reflected waves originating from different areas of the part 1 simultaneously, which makes it possible to inspect the part more rapidly.

The surfaces σi are advantageously positioned along a line or even on a matrix with n rows and p columns.

To implement the method according to the disclosed embodiments, appropriate ultrasound probes are advantageously used. Such probes use conventional technologies for ultrasound probes as for their control means, for example probes using piezoelectric components to emit the incident wave and to measure the characteristics of the reflected waves.

Such probes 20 according to the disclosed embodiments comprise an active surface with an ultrasound emission area 21 with large dimensions and an ultrasound reception area 23 with relatively small dimensions placed roughly in the middle of the active surface of the probe 20.

The reception area 23 comprises one or more ultrasound receivers 22, the measurement surface of each corresponding to the surfaces σi of the method described.

Figure 5A:
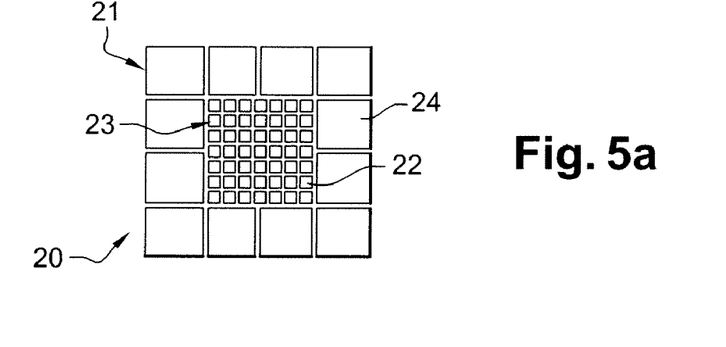
FIGS. 5a, 5b, 5c: exemplary two-dimensional probe architectures for implementing the method.

FIG. 5a illustrates a first exemplary arrangement of the ultrasound elements of a probe. The probe comprises a central measurement area 23 with an arrangement of 7 rows by 7 columns (by way of illustration) of piezoelectric elements 22 of small dimensions able to operate in an ultrasound emission mode and in an ultrasound reception mode. This central area 23 is surrounded by a peripheral area 21 comprising piezoelectric elements 24 able to operate in an ultrasound emission mode such that the total surface of the probe is substantially greater than that of the measurement area 23, twice the width and length for example, having the effect of multiplying the active surface of the emitting probe by four. The elements 24 of the peripheral area, which are used only to emit ultrasounds, are, for example, the same as those of the central area, but preferably as illustrated in FIG. 5a they are elements of proportionally large dimensions compared to the elements 22 of the central area which makes it possible to reduce the number of electronic channels used to inspect these elements.

When the probe 20 is used to implement the method, in a first step all the elements of the probe, the peripheral elements 24 and the elements 22 of the central area 23, are used in emission mode to generate a wide ultrasound wave 3. In a second step, the reflected waves 4, 5 are measured by the elements 22 of the central measurement area 23. When, as in the example illustrated, the central measurement area 23 comprises a matrix of measurement elements 22, it is possible to simultaneously carry out the measurement of the characteristics of the part to be inspected for as many points as there are measurement elements, with electronic circuitry receiving the signals received from the various measurement elements in parallel without multiplexing, and so significantly increase the speeds with which the part can be swept with the probe.

Figure 5B:
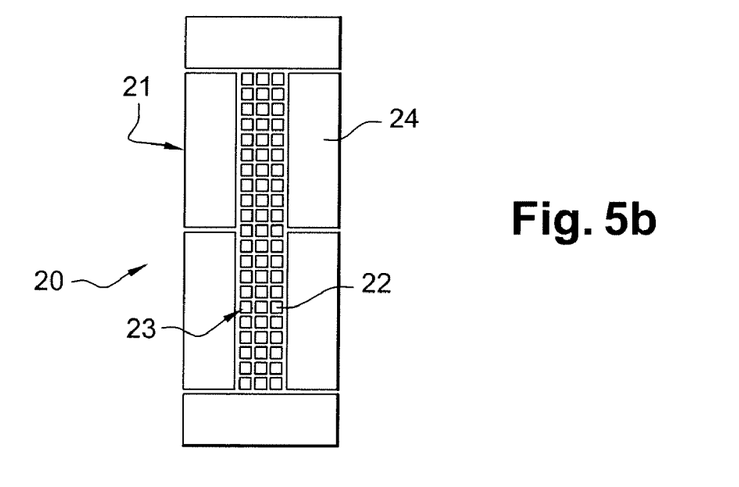
Figure 5C:
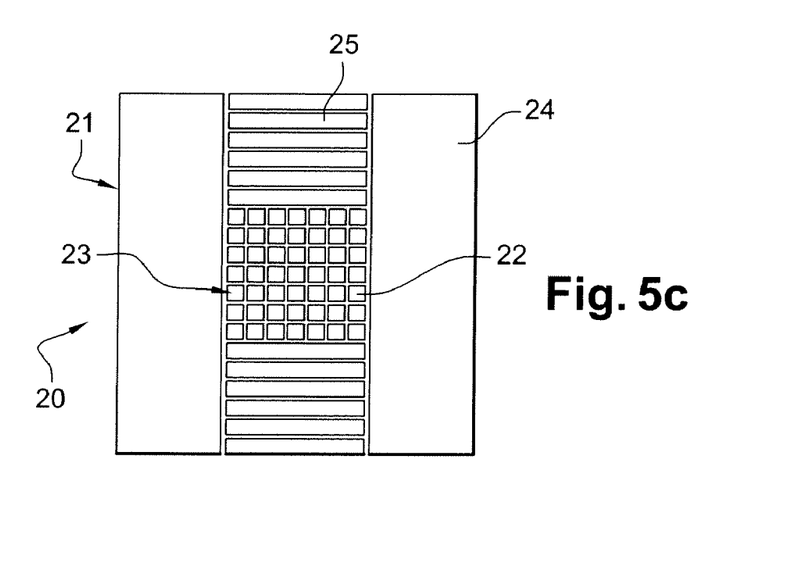

The probe is advantageously adapted as illustrated in FIGS. 5b and 5c according to the geometrical characteristics of the parts to be inspected.

FIG. 5b illustrates a probe that is relatively similar in its form to the example of FIG. 5a, but which has a favored direction that is suitable for inspecting elongated parts.

FIG. 5c illustrates a probe in which the peripheral area comprises elements 25 of small dimensions along a favored axis for generating an ultrasound wave whose wavefront can be adapted to curves of the surfaces of the part to be inspected. The generation of a curved wavefront is obtained in a known way by applying delays to the excitation pulses of the various ultrasound wave emission elements. The determination of the phase delays or advances to be applied to obtain the desired curve or curves is, for example, established by calculation based on the theoretical dimensions of the part to be inspected or even is obtained by performing a preliminary ultrasound measurement by means of the probe.

The method and the probes according to the disclosed embodiments, by reducing the positioning constraints of the probes relative to the parts to be inspected, make it possible to carry out the inspection of the parts by ultrasounds by simplifying the costly probe displacement devices. They also make it possible to inspect parts that have non-parallel faces without having to multiply the measurements.

The method and the probes according to the disclosed embodiments are applicable in particular to the inspection of structural parts made of composite materials such as the complex parts made of composite materials used in the manufacture of aircraft structures.

The invention claimed is:

1. Non-destructive ultrasound inspection method for inspecting a part with a front face and a rear face, the method comprising:
   immersing the part to be inspected in an ultrasonic conducting medium;
   emitting in said medium an incident ultrasonic beam oriented along an incident axis with a first section $\Sigma$ orthogonal to the incident axis of the incident ultrasonic beam in the direction of the front face of the part;
   measuring reflected waves by the part within at least one second section $\sigma$, said second section $\sigma$ being:
   substantially smaller than first section $\Sigma$ of the incident ultrasonic beam;
   located in space such that it is inside a volume where waves of the incident ultrasonic beam are reflected by the front face and inside a volume where waves of the incident ultrasonic beam are reflected by the rear face.

2. Method according to claim 1, comprising measuring the reflected waves simultaneously on several second sections $\sigma 1, \sigma 2, \ldots \sigma n$.

3. Method according to claim 1, comprising measuring the reflected waves close to the axis of the incident beam.

4. Method according to claim 1, comprising orienting the incident axis orthogonally to a theoretical surface of the part.

5. Method according to claim 1, further comprising conforming a wavefront of the incident ultrasonic beam in accordance with curves of surfaces of the part being inspected.

6. Method according to claim 2, comprising measuring the reflected waves on several second sections $\sigma 1, \sigma 2, \ldots \sigma n$, and storing characteristics of the reflected waves for off-line processing.

7. Method according to claim 2, comprising measuring the reflected waves simultaneously on several second sections $\sigma 1, \sigma 2, \ldots \sigma n$, and combining characteristics of the reflected waves in real time.

8. Method according to claim 5, comprising measuring the curves of the surfaces of the part to be inspected by ultrasound before conforming the wavefront.

* * * * *

UNITED STATES PATENT AND TRADEMARK OFFICE
CERTIFICATE OF CORRECTION

PATENT NO. : 7,934,425 B2  
APPLICATION NO. : 11/930276  
DATED : May 3, 2011  
INVENTOR(S) : Barbeau et al.

Page 1 of 1

It is certified that error appears in the above-identified patent and that said Letters Patent is hereby corrected as shown below:

On the Title page, add: Item --30 Foreign Application Priority Data: October 31, 2006 (FR) 06 54651--

Signed and Sealed this
Twentieth Day of December, 2011

David J. Kappos
*Director of the United States Patent and Trademark Office*